(12) United States Patent
Rogers et al.

(10) Patent No.: US 7,780,794 B2
(45) Date of Patent: Aug. 24, 2010

(54) MEDICAL IMPLEMENT CLEANING DEVICE

(75) Inventors: Bobby E. Rogers, San Diego, CA (US);
Paul DiPerna, San Clemente, CA (US)

(73) Assignee: Ivera Medical Corporation, San Diego, CA (US)

( * ) Notice: Subject to any disclaimer, the term of this patent is extended or adjusted under 35 U.S.C. 154(b) by 591 days.

(21) Appl. No.: 11/705,805

(22) Filed: Feb. 12, 2007

(65) Prior Publication Data

US 2008/0019889 A1   Jan. 24, 2008

Related U.S. Application Data

(60) Provisional application No. 60/832,437, filed on Jul. 21, 2006, provisional application No. 60/850,438, filed on Oct. 10, 2006.

(51) Int. Cl.
*B08B 17/04* (2006.01)
*A61M 39/16* (2006.01)

(52) U.S. Cl. .............................. 134/6; 15/97.1; 604/533

(58) Field of Classification Search .............. 15/104.92, 15/104.93; 134/6; 604/533
See application file for complete search history.

(56) References Cited

U.S. PATENT DOCUMENTS 4,752,983 A   6/1988 Grieshaber

| 6,116,468 A * | 9/2000 | Nilson ........................ 222/108 |
| 6,250,315 B1 | 6/2001 | Ernster |
| 2005/0214185 A1 | 9/2005 | Castaneda |
| 2007/0112333 A1 | 5/2007 | Hoang et al. |

FOREIGN PATENT DOCUMENTS

WO   2007137056   11/2007

OTHER PUBLICATIONS

PCT Form ISA 220, PCT Notification of Transmittal of the International Search Report and the Written Opinion of the International Searching Authority, dated Jul. 22, 2009, issued in connection with corresponding PCT Application PCT/US2008/053744.

* cited by examiner

*Primary Examiner*—Michael Kornakov
*Assistant Examiner*—Natasha Campbell
(74) *Attorney, Agent, or Firm*—Mintz, Levin, Cohn, Ferris, Glovsky & Popeo, PC (57) ABSTRACT

A cleaning device for a medical implement is disclosed. The cleaning device includes a cap having an opening to an inner cavity, the opening being adapted to receive a site of the medical implement. The cleaning device further includes a compressible cleaning material that contains a cleaning agent prior to receipt of the site of the medical implement, i.e. the cleaning material is pre-loaded with the cleaning agent. The compressible cleaning material is at least partially secured in the inner cavity and adapted to swab and clean the site with the cleaning agent.

24 Claims, 7 Drawing Sheets

MEDICAL IMPLEMENT CLEANING DEVICE

CROSS REFERENCE TO RELATED APPLICATIONS

The present patent application claims priority under 35 U.S.C. §119 to U.S. Provisional Patent Application Ser. No. 60/832,437 filed on Jul. 21, 2006, entitled "DISINFECTING CAP", and to U.S. Provisional Patent Application Ser. No. 60/850,438 filed on Oct. 10, 2006, entitled "DISINFECTING CAP" the entire disclosures of which are incorporated by reference herein.

BACKGROUND

Within the medical field, and in particular the area of infusion of fluids or aspiration of fluids to or from a patient, there is a need to prevent the transmission of pathogens into or onto a patient from a potentially contaminated surface of a medical implement, or "site". Such pathogens include microorganisms such as bacteria and viruses. The transmission of pathogens into a patient may result in an infection that could be life threatening. Specific to healthcare settings, the term "nosocomial infection" describes those infections that originate from or occur in a hospital or hospital-like setting. In the U.S., nosocomial infections are estimated to occur in at least 5% of all acute care hospitalizations. The estimated incidence is more than two million cases per year, resulting in an added expenditure in excess of $4.5 billion. Nosocomial infections are estimated to more than double the mortality and morbidity risks of any admitted patient, and likely result in about 90,000 deaths a year in the United States. Common sites for such transmissions are found on such medical implements as a luer port, vial, needle free valve, or an injection port of a vessel, tubing, or catheter. Even non-intrusive medical implements such as stethoscopes can transmit pathogens to a patient. The incidence of infection in patients is presently numerous and increasing, and Infection Control Practitioners (ICP's) often cite improper cleaning of sites as a major source of these infections.

Traditionally, cleaning a potentially contaminated surface includes a protocol of alcohol swabbing prior to making the necessary connections to the site. Today alcohol swabs, a small pad of cotton gauze soaked in isopropyl alcohol, are packed individually in a foil package. The foil package is relatively inexpensive, and is used to retain the alcohol within the package and to prevent evaporation. Properly used, the package is opened at or near the site to be swabbed. With gloved hands, the pad is removed by a healthcare provider and wiped across the top and side surfaces of the site, and the pad and foil package are discarded. The site should be allowed to dry, usually twenty to thirty seconds, immediately prior to making any connection. This "drying" period is important: when alcohol dries, it breaks open the cellular walls of microorganisms, thereby killing them.

Unfortunately, because of increased duties and responsibilities, shrinking nursing staffs, and inadequate training, swabbing is often overlooked or is poorly executed. A poorly swabbed site can carry microorganisms that, if allowed to enter a patient's body, can cause serious infection. In addition, supervisory oversight is nearly impossible, because unless a supervisor can actually observe the swabbing being performed, the supervisor cannot know whether or not it was done properly or performed at all. Further, without at least a sufficient microscopic examination for microbial residue, there may be no evidence of an alcohol swab being performed. Thus, a need exists for an apparatus and technique for cleaning a site on a medical implement prior to contact with a patient, and which will eliminate technique-related issues and training issues, and provide an unequivocal indicator that a site is clean prior to accessing a patient's vascular system.

SUMMARY

A cleaning device, system and method for a medical environment is disclosed. In one aspect, the cleaning device includes a cap having an opening to an inner cavity, the opening being adapted to receive a site of the medical implement. The cleaning device further includes a compressible cleaning material that contains a cleaning agent prior to receipt of the site of the medical implement, i.e. the cleaning material is pre-loaded with the cleaning agent. The compressible cleaning material is at least partially secured in the inner cavity and adapted to swab and clean the site with the cleaning agent.

In another aspect, a cleaning system for a threaded medical implement includes a cap having an inner cavity and an opening to receive a site of the medical implement into the inner cavity. The system further includes a threaded ring connected to the inner cavity at the opening to the cap, and having threads that correspond to threads on the threaded medical implement. The system further includes a cleaning material in the inner cavity adapted to provide radial compression against the threaded medical implement, the cleaning material containing a cleaning agent prior to receipt of the site of the medical implement. The opening is preferably covered by a removable vacuum seal.

In yet another aspect, a method of cleaning a site of a medical implement includes the steps of at least partially saturating a cleaning material with a cleaning agent in an inner cavity of a cap; and contacting a top of the site of the medical implement to a first portion of the cleaning material. The method further includes steps of compressing the first portion of cleaning material with the site of the medical implement to contact a side of the site with a second portion of the cleaning material provided around the first cleaning material, and attaching the cap over the site of the medical implement.

In yet another aspect, a cleaning device for a medical implement includes a cap having an opening to an inner cavity, an inner surface of the opening including one or more threads adapted to receive a site of the medical implement. The cleaning device further includes a cleaning material formed of a compressible material that is at least partially secured in the inner cavity, the cleaning material containing a cleaning agent.

In still yet another aspect, a cleaning system for a medical environment includes a plurality of caps. Each cap includes an inner cavity and an opening to receive a site of the medical implement into the inner cavity, and a cleaning material in the inner cavity adapted to provide radial compression against a site of a medical implement, the cleaning material containing a cleaning agent prior to receipt of the site of the medical implement. The system further includes a seal that covers the opening of each of the plurality of caps, and from which individual ones of the plurality of caps can be selectively removed to be used for cleaning the site of the medical implement.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

In accordance with preferred embodiments, a cleaning device includes a cap having a shape and/or external features to promote easy gripping and a cleaning material in the cap that holds or is in contact with a cleaning agent, such as isopropyl alcohol, for application of the cleaning agent to a site of a medical implement.

The cleaning material can be any substance that can conform, mold or compress in a manner that enables the effective wiping of the site, including the top surface of the site, side surface, and any threads or grooves, if present, and provide the cleaning agent at least at a surface level. Examples of the cleaning material include cotton, open or closed cell foam such as polyethylene foam, or other substance that can hold or carry the cleaning agent. The cleaning agent can be any chemical, substance or material that cleans the site of bacterial or even viral microorganisms, or any carrier that contains such chemical, substance or material. Examples of a cleaning agent include isopropyl alcohol, chlorhexidine, povidone-iodine, hydrogen peroxide, soap, and hydrochloric acid.

The term "medical implement" is used to denote any tool or object that can be used in a medical setting and that can connect to a site cleaning device as described herein according to a number of embodiments. Examples of medical implements include, but are not limited to, access ports on tubing sets (extension sets, T-connectors and IV sets), access ports on catheters (both peripheral and central lines), needle free valves, stopcocks, luer connectors, stethoscopes and other components or devices whereby regular cleaning is desired. Medical implements are commercially available in standard sizes. Thus, the end or opening of a site cleaning device can be provided with fittings to accommodate such standard size medical implements.

The cap of the cleaning device is made of a material that is compatible with the cleaning materials and agents to be used, examples of materials would include, sealed foam, plastic, glass, or metal. The cleaning device may need to undergo sterilization. For securing the cleaning device to another device, the cleaning device can include attachment mechanisms such as "snap-fit" mechanisms or clamps to hold it in place on the other device. Alternatively the cleaning material in the cap may conform to the sides of the medical implement to thereby "grip" and remain secured to the medical implement. The cap also may have threading to secure it in place on a medical implement. The cap may have some cutaway portions on its walls to enable the use of some undercuts during the molding process, and to allow the cleaning material to flex outward both during use. The cap can be made from polyethylene or another material that is stable when in the presence of alcohol or other cleaning agent.

In preferred exemplary embodiments, prior to being applied to a site, and after the cleaning material is provided with a cleaning agent, the opening of the cap is sealed with a foil-based seal or other material suitable for retaining a cleaning agent in the cleaning material and preventing evaporation of the cleaning agent. The cap seal may also be formed in a manner whereby several caps could be attached i.e. a strip, where individual caps can be peeled from the strip in order to be used. These strips of caps can be made conveniently accessible, i.e. hung from intravenous (IV) poles or IV sets, in patient rooms and medication carts, to name just a few. The strips provide the convenience of having several caps available in one location.

The cleaning material in the cap can be an alcohol-soaked piece of gauze, foam or similar cleaning material. The cleaning material can be formed into the general interior shape of the cap from one or more pieces. For instance, the cleaning material can include a ring for circumscriptive coverage and cleaning of the site, and further include a cylinder within the ring for coverage and cleaning on a distal end of the site. A single piece of cleaning material may also be cut or formed to perform the same coverage and cleaning functions as the two pieces described above. The cleaning material may also cover the threads and/or be formed as part of the threads.

In still further embodiments, the cleaning material may be made entirely or partially of the cleaning agent. For example, the cleaning material can be formed of an open cell foam or plastic that is chemically or physically impregnated with a cleaning agent such as povidone or iodine, or isopropyl alcohol.

Figure 1:
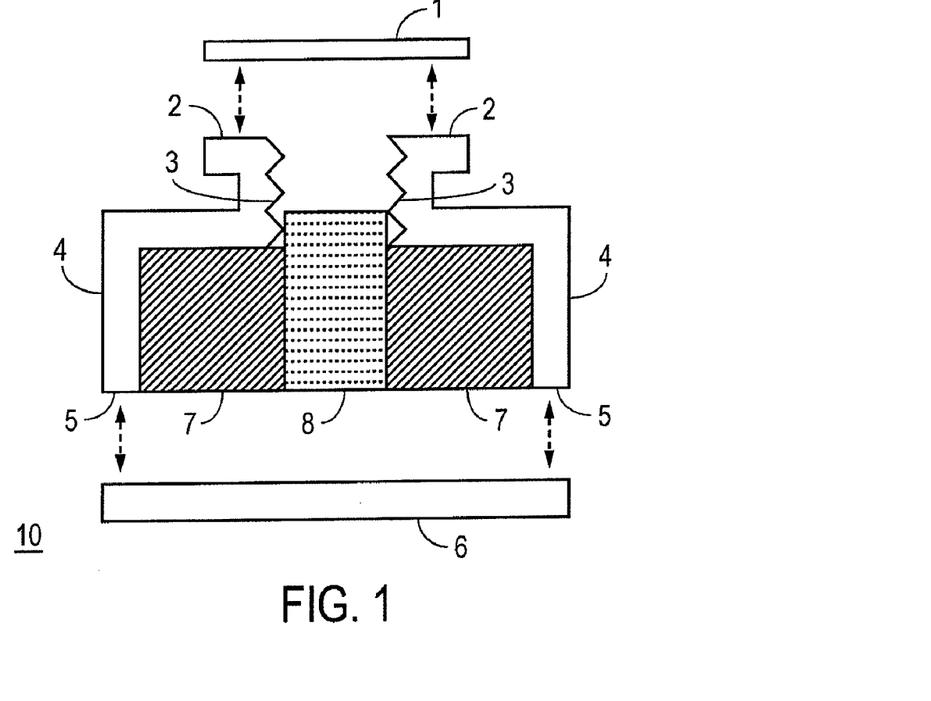
FIG. 1 is a cross-sectional, exploded view of a cleaning device.

To further illustrate and describe these concepts, reference is now made to FIG. 1, which shows a cross-sectional, exploded view of a cleaning device, embodied as a cap 10 with a housing 4 that defines an inner cavity 20 of the cap 10. A foil seal 1 is configured to attach to a sealing surface 2 of the housing 4. The housing 4 further includes internal threads 3. In a preferred exemplary embodiment, the internal threads 3 are sized and arranged to accommodate luer threads, i.e. standardized male threads designed to mate with the female threads on a medical implement to which the cap 10 attaches. The housing 4 also has a mating surface 5 for attachment of a bottom portion 6.

Within housing 4 is a first cleaning material 7. The first cleaning material 7 may be attached to the walls of housing 4 by glue, solvent or some other attachment composition or mechanism, or may be held in the housing 4 by compression or trapped between the bottom portion 6 and housing 4. Ribs or protrusions on the inside of the housing 4 may also be used to prevent the cleaning material 7 from slipping or rotating. The first cleaning material 7 is compressible, and is preferably doughnut-shaped or ring-shaped. The first cleaning material 7 is positioned and configured to compress radially in an outwardly direction to scrub or wipe the circumscriptive surface of the site and the surface of the threads of an inserted medical implement.

A second cleaning material 8 is designed to compress in the axial direction upon insertion of the medical implement and is designed to wipe the distal end and distal surface of the inserted medical implement. The second cleaning material 8 may be attached to the walls of bottom portion 6 by glue, solvent or some other attachment composition or mechanism, or affixed to first material 7 by glue, solvent or some other attachment composition or mechanism. Protrusions on the inside of the bottom portion 6 may also be used to prevent the cleaning material 8 from rotating or removal. The first cleaning material 7 and second cleaning material 8 may be formed from a single piece of compressible cleaning material of cotton, foam or other suitable cleaning material adapted for scrubbing. This single piece may be cut completely or partially cut to achieve a similar effect as two separate pieces of cleaning material.

Figure 2:
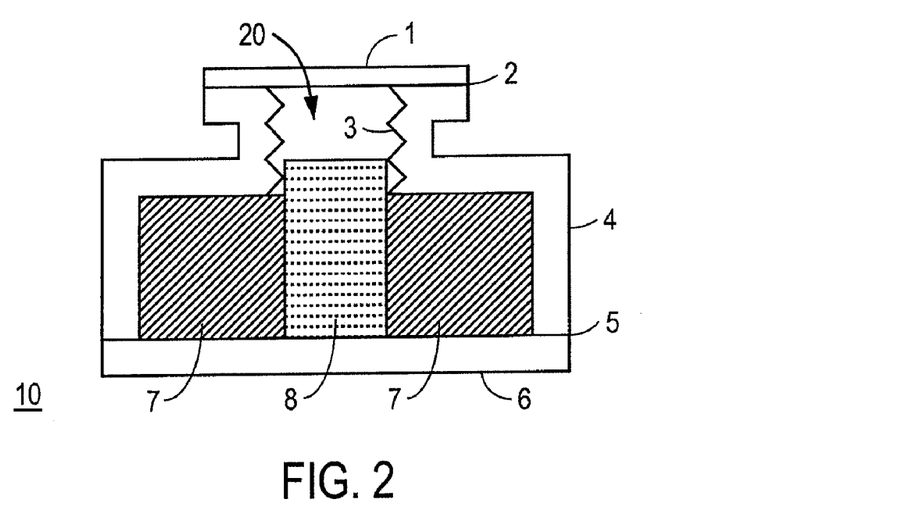
FIG. 2 is a cross-sectional view of an assembled cleaning device.

FIG. 2 illustrates an assembled cap 10. The first and second cleaning materials 7 and 8 in the inner cavity 20 are at least partially saturated with a cleaning agent, such as isopropyl alcohol, or a mix of cleaning agents. The foil seal 1 is then attached to housing 4 at sealing surface 2 by glue, solvent, thermal bonding, etc. A bottom portion 6 is attached to housing 4 at point 5 by glue, welding, solvent, threads or other attachment mechanism or process. With the foil seal 1 and the bottom portion 6 attached to housing 4, the inner cavity 20 is hermetically sealed. The housing 4, bottom portion 6, and first and second cleaning materials 7, 8 are respectively made of a material or cleaning materials that are compatible with the cleaning agent. For instance, if isopropyl alcohol is used for at least part of the cleaning agent, the housing 4 and bottom portion 6 can be constructed of a plastic such as polyethylene. The housing 4 and bottom portion 6 can be formed of a unitary piece of material, as explained further below.

Figure 3:
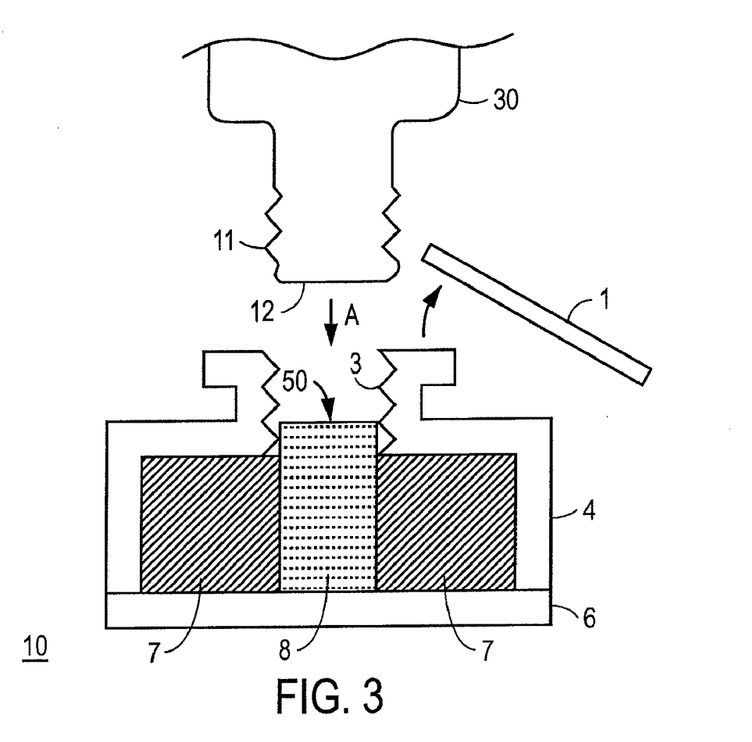
FIG. 3 illustrates operation of a cleaning device for connection to a site of a medical implement.

FIG. 3 illustrates a medical implement 30 moving toward housing 4, in a direction A, which should be recognized as a reference only, and that the housing 4 can likewise be moved toward the medical implement 30. The foil seal 1 is removed from housing 4. In alternative embodiments, the foil seal 1 can be a foil pouch or other sterilized material that would inhibit evaporation of the cleaning agent. A distal end surface 12 of the medical implement 30 is eventually contacted with the upper surface 50 of the second cleaning material 8.

Figure 4:
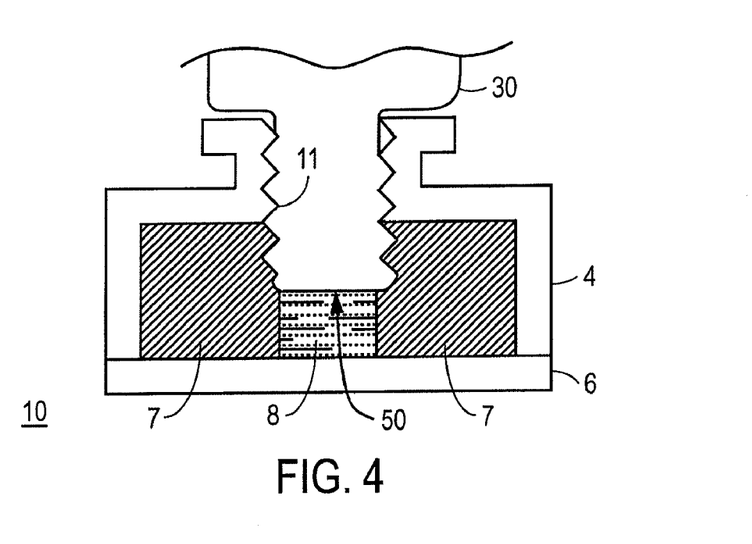
FIG. 4 illustrates a cleaning device connected to a medical implement and cleaning a site of the medical implement.

As the medical implement 30 continues in direction A, it axially compresses second cleaning material 8 continuing to clean surface 12 with surface 50. This movement also begins to radially compress the first cleaning material 7 and to conform the first cleaning material 7 with, and begin scrubbing, threads 11. The cleaning materials 7 and 8 contain the cleaning agent so as to perform a thorough cleaning of the area about the threads 11 and the surface 12. As threads 11 of the medical implement 30 continue to be rotationally inserted into the threads 3 of the housing, the distal end surface 12 is automatically scrubbed by surface 50 of the second cleaning material 8 and cleaned by cleaning agent held therein, and at least a portion of the side and threads 11 of the medical implement 30 are automatically scrubbed by radial compression of the first cleaning material 7 and cleaned by a cleaning agent held therein. FIG. 4 illustrates the disinfecting cap 10 with a fully inserted medical implement 30.

The cap 10 can be removed immediately from the medical implement 30 after use, or be kept in place. If the cap 10 is removed the medical implement 30 surfaces 11 and 12 will be clean and ready for use upon the drying of the cleaning agent. If the cap 10 is kept secured to medical implement 30, the cleaning agent in cap 10 will evaporate over time thereby destroying any microorganisms on the surfaces 12 and 11 of medical implement 30. The cap 10 then maintains the surfaces 11 and 12 of medical implement 30 in a clean and ready-to-access state by eliminating any forms of touch contamination.

Figure 5:
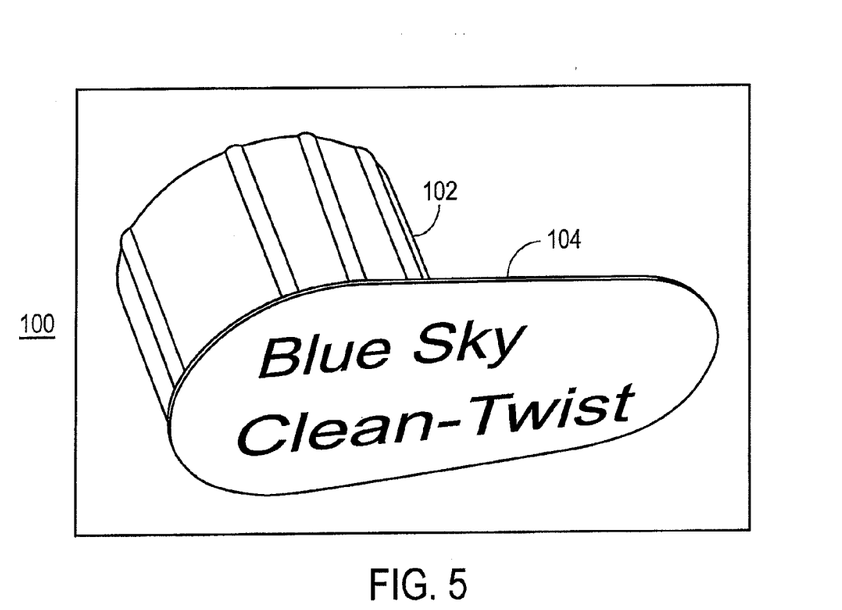
FIG. 5 shows another embodiment of an assembled cleaning device.
Figure 6:
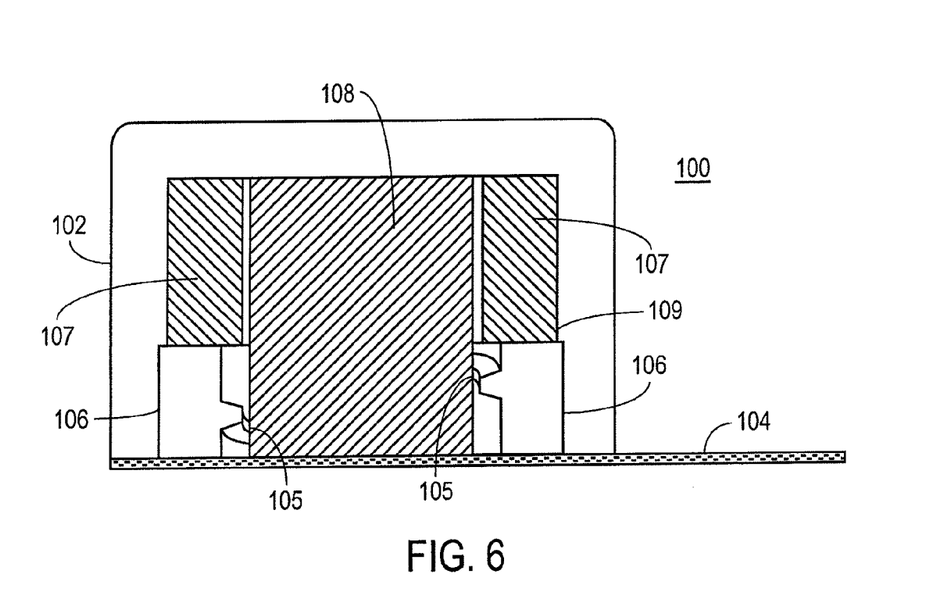
FIG. 6 is a cross-sectional view of an assembled cleaning device in accordance with an embodiment.

FIGS. 5-10 illustrate an alternate embodiment of a cleaning device 100. FIG. 5 is a perspective view of the cleaning device 100 formed of a cap 102 with a seal 104 that is connected to and covers the opening of the cap 102. The cap 102 can have a number of gripping ridges or projecting members for ease of use. FIG. 6 is a cross-sectional view of the cleaning device 100. The cap 102 forms an inner cavity with one opening that is large enough to receive a site of a medical implement. The seal 104 is affixed to the opening and is preferably entirely removable. In other embodiments, the seal 104 is permanently affixed, and is simply punctured by insertion of a site of a medical implement.

The cap 102 houses a threaded ring 106 proximate to the opening. The threaded ring 106 includes one or more threads 105 and is adapted to receive the site of the medical implement to be disinfected, and thus defines the size and shape of the opening. This embodiment is advantageous because it creates a single circumferential seal point, seal 104 to the opening of cap 102.

In some embodiments, the cap 102 and threaded ring 106 are formed of a unitary piece of material or cleaning material. In other embodiments, the threaded ring 106 fits into a groove 109 that is formed in the inside edge surface of the cap 102 near the opening. In this latter configuration, the groove 109 maintains the position of threaded ring 106 near the open end of the cap where the threaded ring top surface may be flush with or slightly recessed from the cap open end walls, and the threaded ring 106 may also include or create with the cap wall a small vent aperture or opening to allow evaporation of a cleaning agent in the cap 102. The threaded ring 106 can be mechanically kept from rotating with internal ribs or protrusions in cap 102 or groove 109. Threaded ring 106 may be held in place within grove 109 and cap 102 by glue, welding, snap-fit, solvent bonding or any other mechanism or composition known to those of requisite skill.

The cleaning device 100 further includes a first cleaning material 10 that holds the cleaning agent, such as isopropyl alcohol, and a second cleaning material 108 that also holds or is at least partially saturated by the cleaning agent. In preferred exemplary embodiments, the first cleaning material 107 is formed as a hollow cylinder or ring positioned between the threaded ring 106 and the top inside surface of the cap 102, and is adapted for radial compression against a site that is inserted into the cap 102 or over which the cap 102 is placed. In some embodiments, the second cleaning material 108 is formed as a solid cylinder and positioned within the hollow space of the first cleaning material 107, and is adapted for axial compression against a leading edge of the site that is inserted into the cap 102 or over which the cap 102 is placed. In other embodiments, cleaning materials 107 and 108 can be made of a single piece of material and cut or formed so as to achieve the same result as described above. The cleaning agent is provided to the cleaning materials 107, 108 prior to the opening being covered with the seal 104.

Figure 7:
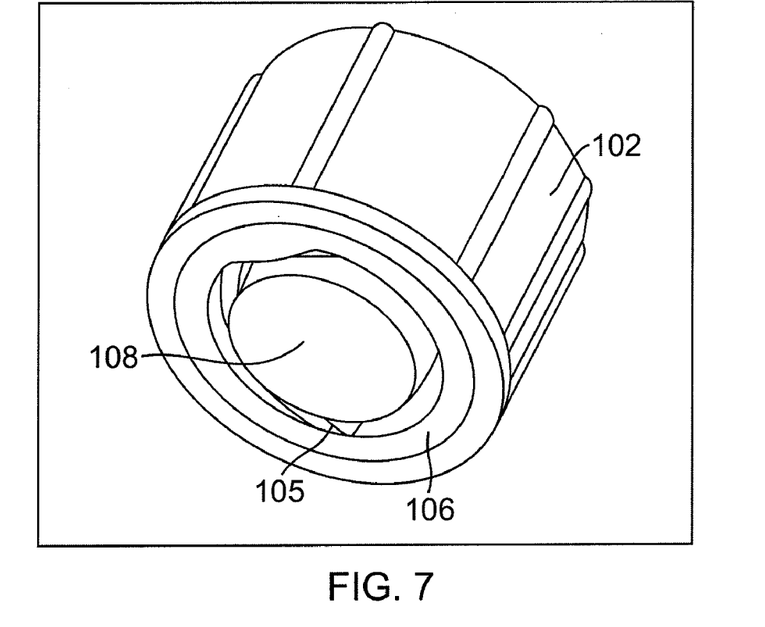
FIG. 7 is a perspective view of another cleaning device.
Figure 8:
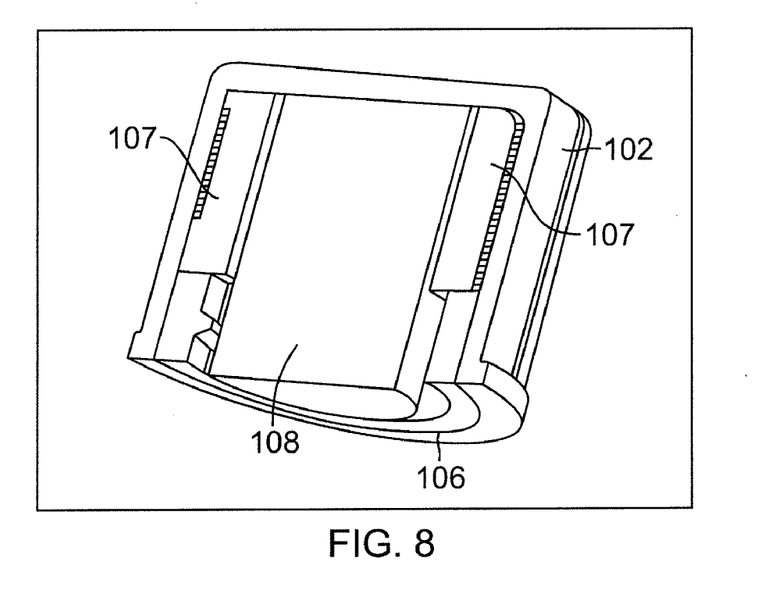
FIG. 8 is a cross section of a cleaning device.
Figure 11:
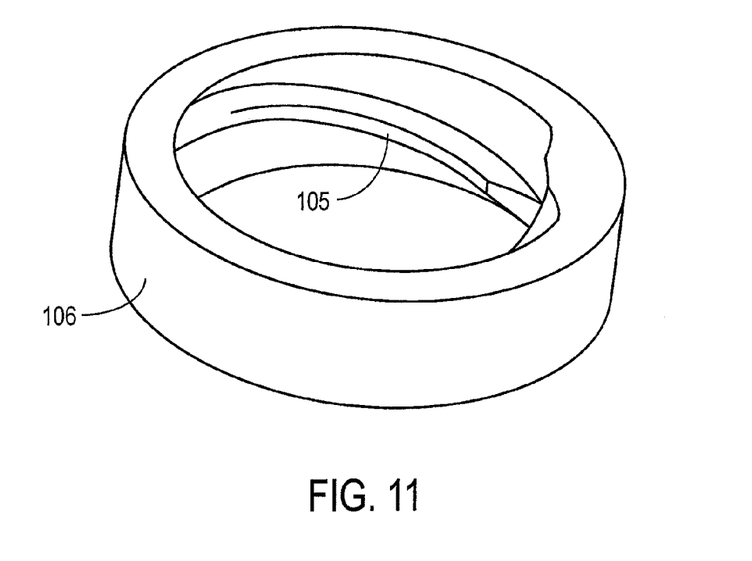
FIG. 11 is a perspective view of a ring that attaches to a corresponding structure of a medical implement.

FIG. 7 is a bottom perspective view and FIG. 8 is a cross-sectional view of the cleaning device 100 with the seal 104 removed, showing the cap 102, threaded ring 106 that sits within the cap 102, and the second cleaning material 108 inside the cap 102. The second cleaning material 108 can extend to and slightly beyond the opening of the cap 102. FIG. 8 further shows the first cleaning material 107 that circumscribes the second cleaning material 108 and being positioned between the threaded ring 106 and the top inner surface of the cap 102. FIG. 11 illustrates an example of the threaded ring 106 and its threads 105. An attribute of this embodiment of the threaded ring 106 shown in FIG. 11 is that there are only two opposing threads that travel 180 degrees before terminating. This enables the molding of threaded ring 106 without the use of a screw to create the thread feature in an injection molding tool. The threaded ring 106 can also be produced with an injection molding tool utilizing a screw.

Figure 9:
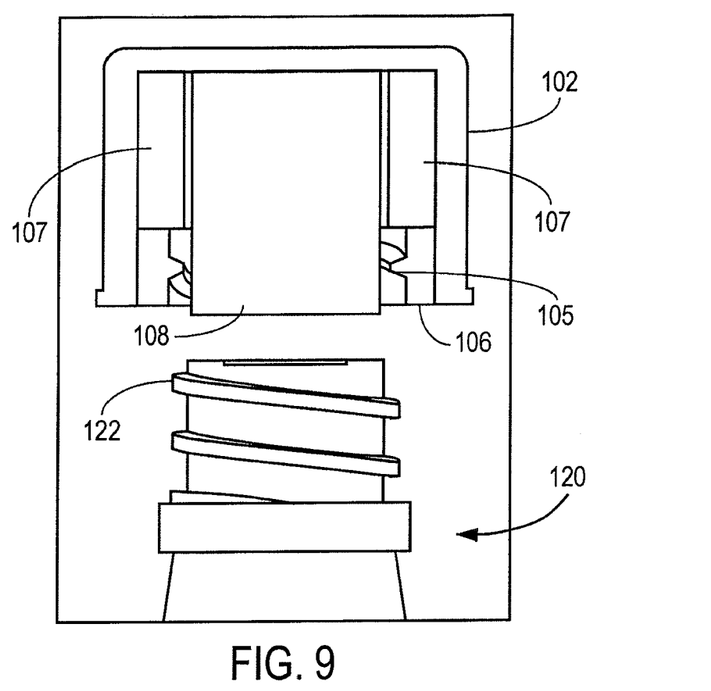
FIGS. 9 and 10 show a cleaning device being used to clean a site of a medical implement.
Figure 10:
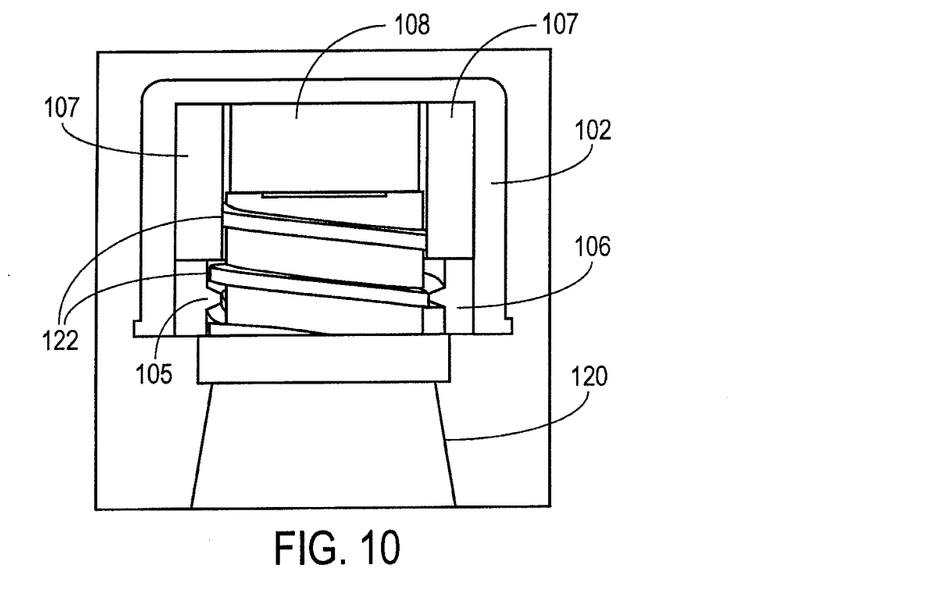

FIG. 9 illustrates the cleaning device 100 about to make contact with a site 120 of a medical implement. As discussed above, the site 120 can be a luer port, a, a needle free valve, an injection port of a vessel, or other medical implement that needs to be cleaned prior to use with a patient. In some embodiments, the site 120 can include a set of threads 122 that correspond to the threads 105 in the threaded ring 106 of the cleaning device 100. The cleaning materials 107 and 108 are preloaded with a cleaning agent, before removal of the seal and contact by the site 120. Accordingly, as shown in FIG. 10, the site 120 makes contact with the cap 102 by a screwing motion relative to the cap 102. The second cleaning material 108 is compressed axially and swabs against the leading edge of the site 120, while the first cleaning material 107 is compressed radially and swabs against sides of the site 120.

FIG. 11 illustrates the molded thread ring 106 with two opposing threads 105 that traverse opposing 180 degree portions of the ring. This design enables the thread ring 106 to be molded without the use of a screw that is typically used to create threaded parts in a molding process. Thus the threaded ring 106 can be manufacture very inexpensively. The threaded ring 106 can also clean some of the threads when the cap is placed into position, and may or may not cover all the threads. In some embodiments, the threaded ring 106 can be molded from the cleaning material, or the cleaning material is formed only of the threaded ring 106. In such embodiments, the cleaning may only occur on threads of the site and in an axial direction.

Figure 12:
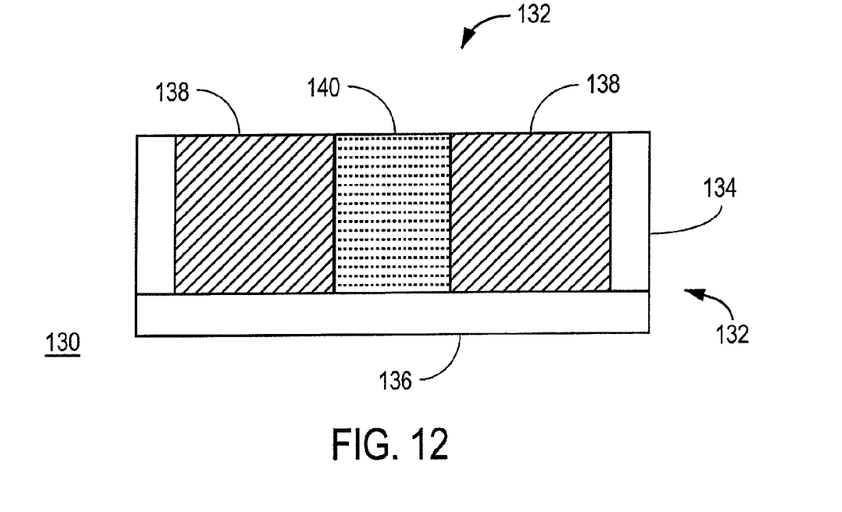
FIG. 12 is a cross sectional view of another alternative embodiment of a cleaning device.

FIG. 12 shows an alternative embodiment of a cleaning device 130 having a cap 132 that is filled with a cleaning material. The cap 132 has side walls 134 and a top 136 that define an inner cavity with an opening 132. The cleaning material includes at least a first cleaning material 138, such as cotton or foam, that delivers a cleaning agent. The cleaning material can include a second cleaning material 140 to hold more cleaning agent. In some embodiments, the second cleaning material 140 can be circumscribed by the first cleaning material 138. Alternatively, the first cleaning material 138 can completely envelope the second cleaning material 140, each providing their own compressibility and capacity to hold a cleaning agent. Still, in other embodiments, the first and second cleaning materials 138, 140 can be formed of a single piece of material. The cleaning material(s) are filled at least partially with a cleaning agent, prior to sealing of the opening 132 with a seal and closure of the inner cavity.

Figure 13:
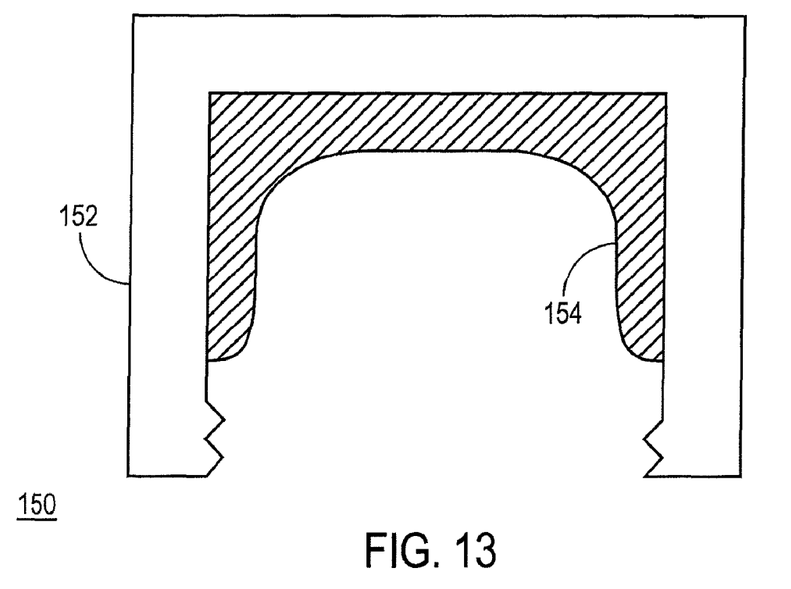
FIG. 13 shows yet another alternative embodiment of a cleaning device.

FIG. 13 shows an alternate embodiment of a cleaning device 150. In this embodiment, the cleaning device 150 includes a housing 152 that is formed as a threaded cap. The inner surface of the housing 152 is covered, at least in part, by a cleaning layer 154 that is bonded to the inner surface of the housing 152. The cleaning layer 154 can be a cleaning material such as cotton, foam, or other porous and pliable material that suitably holds and/or delivers a cleaning agent such as isopropyl alcohol. The cleaning layer 154 is sized and positioned inside the housing 152 so as to be able to swab the top and a portion of the sides of a part of a medical implement that is inserted therein, or over which the housing 152 is placed. Accordingly, the cleaning layer 154 can have any thickness or compressibility.

Figure 14:
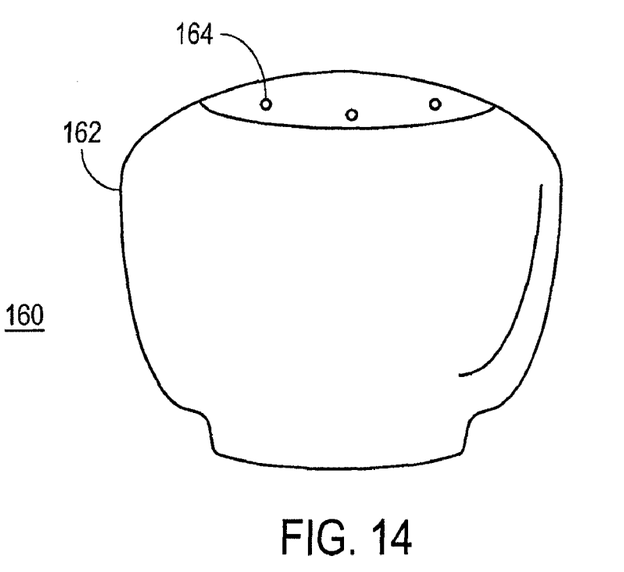
FIG. 14 shows a cap of a cleaning device in accordance with some embodiments.

FIG. 14 shows yet another alternative embodiment of a cleaning device 160, illustrating an outer view of a rounded housing 162 for an expanded inner chamber to hold more cleaning agents or cleaning materials that hold such agents. Holes 164 in the housing 162 can promote evaporation of the cleaning agent, particularly when the housing covers a site of a medical implement to be disinfected. The location of the vent holes is variable and the vent holes can also be sealed with a filter type membrane that permits the drying of the cleaning agents but does not allow entry of microorganisms or fluid.

The use of the various implementations and embodiments above entails the following: the healthcare worker would, with gloved hands, open the foil package and place this cap over the site of a medical implement to be cleaned. Upon placement the alcohol soaked cleaning material wipes all of the port's surfaces. This wipe could be accomplished by either a turning motion (if threads are used) or by simply pushing the cap onto the port. In this way the cap eliminates errors in the practice of swabbing due to poor training or excessive workloads. The cap would then remain secured in place by threads, mechanical tension provided by the foam, cotton, etc., snaps or some other mechanism. A cap in place on a medical implement is a positive indication that a desired site of the medical implement is clean. A vibrant color may be used to allow instant visualization of a cap's presence from a door or hallway. ICP's can review compliance by merely observing sites to see whether or not a cap is in place. The cap could remain in place for periods of up to three days or more. For extended periods the alcohol will likely evaporate, which assures that the site is clean. With the cap in place, it continues to keep the site clean even after the alcohol has evaporated.

Although a few embodiments have been described in detail above, other modifications are possible. For instance, any of the embodiments described above may be sized and scaled for a particular medical implement, such as a stethoscope. Other embodiments may be within the scope of the following claims.

What is claimed is:

1. A cleaning device for a medical implement, the cleaning device comprising:
   a cap having a first opening to an inner cavity, the opening being adapted to receive a site of the medical implement
   a threaded ring connected to the cap at a periphery of the opening to the inner cavity, the threaded ring providing threading;
   a compressible cleaning material that contains a cleaning agent prior to receipt of the site of the medical implement, the compressible cleaning material at least partially secured in the inner cavity and adapted to swab and clean the site with the cleaning agent; and
   an additional opening in the cleaning device formed between an outside edge of the threaded ring and an inside edge of the inner cavity to allow evaporation of the cleaning agent from the inner cavity and to inhibit a vacuum in the cap when the first opening receives the site of the medical implement.

2. A cleaning device in accordance with claim 1, wherein the cleaning material includes a first cleaning material that forms a ring in the inner cavity, and a second cleaning material that forms a cylinder within the first cleaning material.

3. A cleaning device in accordance with claim 1, wherein the cap includes an outer surface having a plurality of vertical ridges.

4. A cleaning device in accordance with claim 1, further comprising a removable seal connected to the cap over the opening to the inner cavity.

5. A cleaning system for a threaded medical implement, the cleaning system comprising:
   a cap having an inner cavity and an opening to receive a site of the medical implement into the inner cavity;
   a threaded ring connected to the inner cavity at the opening to the cap, and having threads that correspond to threads on the threaded medical implement;
   a cleaning material in the inner cavity adapted to provide radial compression against the threaded medical implement, the cleaning material containing a cleaning agent prior to receipt of the site of the medical implement; and
   one or more vent holes between the threaded ring and the inner cavity at the opening to the cap, the one or more vent holes to permit drying the cleaning agent and to inhabit a vacuum in the inner cavity to support mechanical tension by the threads on the threaded medical implement.

6. A cleaning system in accordance with claim 5, wherein the cleaning material is further adapted to provide axial compression against the threaded medical implement.

7. A cleaning system in accordance with claim 5, wherein the cap and the threaded ring are formed of a unitary piece of material.

8. A cleaning system in accordance with claim 6, wherein the cleaning material is formed of a first cleaning material to provide the radial compression against the threaded medical implement, and a second cleaning material to provide the axial compression against the threaded medical implement.

9. A cleaning system in accordance with claim 5, wherein the cleaning agent includes isopropyl alcohol.

10. A cleaning system in accordance with claim 5, wherein the cap includes an outer surface having a plurality of vertical ridges.

11. A cleaning system in accordance with claim 5, further comprising a removable seal connected to the lower edge of the cap to cover the opening to the inner cavity.

12. A method of cleaning a site of a medical implement, the method comprising:
   at least partially saturating a cleaning material with a cleaning agent in an inner cavity of a cap that includes an opening to the inner cavity and at least one other aperture to the inner cavity the cap further including a removable seal that encloses the opening and the at least one other aperture; removing the seal from the opening and the at least one other aperture;
   contacting a top of the site of the medical implement to a first portion of the cleaning material;
   compressing the first portion of cleaning material with the site of the medical implement to contact the site with the cleaning agent in the cleaning material provided around the first cleaning material;
   attaching the cap over the top of the site of the medical implement; and
   evaporating the cleaning agent through the at least one other aperture to the inner cavity as the cap is attached over the top of the site.

13. A cleaning device for a medical implement, the cleaning device comprising:
   a cap having a first opening to an inner cavity, an inner surface of the first opening including one or more threads adapted to receive a site of the medical implement;
   a cleaning material formed of a compressible material that is at least partially secured in the inner cavity, the cleaning material containing a cleaning agent;
   a second opening in the cap to allow evaporation of the cleaning agent from the inner cavity and to inhibit a buildup of pressure in the cap when the cleaning material is compressed by the site of the medical implement and a removable covering that covers the first opening and the second opening to the inner cavity prior to coupling the threads of the cap with the site of the medical implement via the first opening.

14. A cleaning device in accordance with claim 13, wherein the cleaning material is adapted to provide radial compression against the site of the medical implement for radial swabbing of the site.

15. A cleaning device in accordance with claim 13, wherein the cleaning material is adapted to provide axial compression against the site of the medical implement for axial and rotational swabbing of the site of the medical implement when the site is rotated into the first opening of the cap.

16. A cleaning device in accordance with claim 13, wherein the compressible material includes an open-cell foam.

17. A cleaning device in accordance with claim 13, wherein the cleaning material includes a first cleaning material to provide the radial compression against the site of the medical implement, and a second cleaning material to provide the axial compression against the site of the medical implement.

18. A cleaning device in accordance with claim 13, wherein the cleaning material is preloaded with the cleaning agent prior to a seal being applied to the first and second openings of the cap.

19. A cleaning system for a medical environment, the cleaning system comprising:
   a plurality of caps, each cap having:
      an inner cavity and an opening to receive a site of the medical implement into the inner cavity; and
      a cleaning material in the inner cavity adapted to provide axial compression against a site of a medical implement, the cleaning material containing a cleaning agent prior to receipt of the site of the medical implement; and a threaded ring connected to the inner cavity at the opening to the cap, the threaded ring having threads that correspond to threads on the medical implement; and
      at least one evaporation vent in a wall of the cap between the threaded ring and the inner cavity at the opening to allow evaporation of the cleaning agent upon receipt of the site of the medical implement; and
   a seal that covers the opening of each of the plurality of caps, and from which individual ones of the plurality of caps can be selectively removed to be used for cleaning the site of the medical implement.

20. A cleaning device for a medical implement, the cleaning device comprising: a cap having an opening to an inner cavity, the opening for receiving a site of the medical implement; a threading at a periphery of the opening to the inner cavity; a compressible cleaning material that contains a cleaning agent, the compressible cleaning material at least partially secured in the inner cavity and adapted to swab and clean the site of the medical implement with the cleaning agent; at least one second opening proximate the opening to the inner cavity to allow evaporation of the cleaning agent from the inner cavity and to inhibit a vacuum in the cap when the opening receives the site of the medical implement; and a removable seal attached to the cap at the opening to cover the opening and the second opening, and to maintain the compressible cleaning material and cleaning agent within the inner cavity prior to receipt of the site of the medical implement.

21. The cleaning device in accordance with claim 20, wherein the second opening is formed by a gap in the threading.

22. The cleaning device in accordance with claim 20, wherein the second opening is formed by a gap between an outside edge of a threaded ring connected to the cap at the opening, and an inside edge of the inner surface of the cap.

23. A cleaning device for a medical implement, the cleaning device comprising: a cap having an opening to an inner cavity, the opening being sized for receiving a site of the medical implement; a compressible cleaning material that contains a cleaning agent, the compressible cleaning material at least partially secured in the inner cavity and adapted to swab and clean the site of the medical implement with the cleaning agent; means for venting the cleaning agent from the compressible cleaning material and the inner cavity, the means for venting being created between the cap and the site of the medical implement when the site of the medical implement is received in the opening of the cap; and a removable seal attached to the cap at the opening to cover the opening and to maintain the compressible cleaning material and cleaning agent within the inner cavity prior to receipt of the site of the medical implement.

24. The cleaning device in accordance with claim 23, wherein the compressible cleaning material is formed to clean both a front face and sides of the site of the medical implement.

\* \* \* \* \*

UNITED STATES PATENT AND TRADEMARK OFFICE
CERTIFICATE OF CORRECTION

PATENT NO. : 7,780,794 C1
APPLICATION NO. : 90/009951
DATED : August 24, 2010
INVENTOR(S) : Bobby E. Rogers et al.

Page 1 of 1

It is certified that error appears in the above-identified patent and that said Letters Patent is hereby corrected as shown below:

In the Claims:

At column 2, line number 4, claim number 12 should read --removing [the] *a* seal [from] *that encloses* [the] *an* opening--

Signed and Sealed this
Nineteenth Day of March, 2013

Teresa Stanek Rea
*Acting Director of the United States Patent and Trademark Office*

(12) EX PARTE REEXAMINATION CERTIFICATE (9104th)
United States Patent
Rogers et al.

(10) Number: US 7,780,794 C1
(45) Certificate Issued: Jun. 26, 2012

(54) MEDICAL IMPLEMENT CLEANING DEVICE

(75) Inventors: Bobby E. Rogers, San Diego, CA (US); Paul DiPerna, San Clemente, CA (US)

(73) Assignee: Ivera Medical Corporation, San Diego, CA (US)

Reexamination Request:
No. 90/009,951, Oct. 3, 2011

Reexamination Certificate for:
Patent No.: 7,780,794
Issued: Aug. 24, 2010
Appl. No.: 11/705,805
Filed: Feb. 12, 2007

Related U.S. Application Data (60) Provisional application No. 60/850,438, filed on Oct. 10, 2006, and provisional application No. 60/832,437, filed on Jul. 21, 2006.

(51) Int. Cl.
*B08B 17/14* (2006.01)
*A61M 39/16* (2006.01)

(52) U.S. Cl. .............................. 134/6; 15/97.1; 604/533
(58) Field of Classification Search .................. None
See application file for complete search history.

(56) References Cited

To view the complete listing of prior art documents cited during the proceeding for Reexamination Control Number 90/009,951, please refer to the USPTO's public Patent Application Information Retrieval (PAIR) system under the Display References tab.

*Primary Examiner* — Terrence Till (57) ABSTRACT

A cleaning device for a medical implement is disclosed. The cleaning device includes a cap having an opening to an inner cavity, the opening being adapted to receive a site of the medical implement. The cleaning device further includes a compressible cleaning material that contains a cleaning agent prior to receipt of the site of the medical implement, i.e. the cleaning material is pre-loaded with the cleaning agent. The compressible cleaning material is at least partially secured in the inner cavity and adapted to swab and clean the site with the cleaning agent.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-11 and 13-24 is confirmed.

Claim 12 is determined to be patentable as amended.

12. A method of cleaning a site of a medical implement, the method comprising:
   [at least partially saturating a cleaning material with a cleaning agent in an inner cavity of a cap that includes an opening to the inner cavity and at least one other aperture to the inner cavity the cap further including a removable seal that encloses the opening and the at least one other aperture;]
   removing [the] *a* seal from *that encloses* [the] *an* opening and [the] at least one other aperture *to an inner cavity of a cap;*
   *exposing a cleaning material in the inner cavity of the cap, the cleaning material being at least partially saturated with a cleaning agent prior to removing the seal;*
   contacting a top of the site of the medical implement to a first portion of the cleaning material;
   compressing the first portion of cleaning material with the site of the medical implement to contact the site with the cleaning agent in the cleaning material [provided around the first cleaning material];
   attaching the cap over the top of the site of the medical implement; and
   [evaporating] *venting* the cleaning agent through the at least one other aperture to the inner cavity as the cap is attached over the top of the site.

* * * * *